United States Patent [19]

Setterstrom et al.

[11] Patent Number: 5,470,311
[45] Date of Patent: Nov. 28, 1995

[54] MICROSPHERE DRUG APPLICATION DEVICE

[75] Inventors: Jean A. Setterstrom; Elliot Jacob, both of Silver Spring; Walter K. Franz, Annapolis, all of Md.

[73] Assignee: The United States of America as represented by the Secretary of the Army, Washington, D.C.

[21] Appl. No.: 248,050

[22] Filed: May 24, 1994

Related U.S. Application Data

[63] Continuation-in-part of Ser. No. 493,597, Mar. 15, 1990, abandoned.

[51] Int. Cl.⁶ ................................................. A61M 37/00
[52] U.S. Cl. ............................ 604/24; 604/140; 604/147; 604/290; 128/200.14
[58] Field of Search ........................... 604/19, 23, 48, 604/49, 68–70, 72, 131, 140, 147, 181, 187, 232, 289, 290, 24; 128/200.14, 200.17, 200.18, 200.21, 200.23; 222/389, 394, 396, 397, 399, 630, 631, 635

[56] References Cited

U.S. PATENT DOCUMENTS

| | | | |
|---|---|---|---|
| 3,540,444 | 11/1970 | Moreland | 604/72 |
| 3,788,315 | 1/1974 | Laurens | 604/70 |
| 4,941,880 | 7/1990 | Burns | 604/143 |
| 5,059,187 | 10/1991 | Sperry et al. | 604/290 |
| 5,064,413 | 11/1991 | McKinnon et al. | 604/70 |
| 5,129,825 | 7/1992 | Discko, Jr. | 433/90 |
| 5,133,701 | 7/1992 | Han | 604/289 |

*Primary Examiner*—Corrine M. Maglione
*Attorney, Agent, or Firm*—John Francis Moran; Anthony T. Lane

[57] ABSTRACT

Apparatus and methods for dispensing medicinals encapsulated in a biodegradable polymer in surgical and other wounds are described. The apparatus, a microcapsule drug applicator, allows the caregiver to implant or spread measured and uniform quantities of microencapsulated medicinals in or on surgical or traumatic wounds to prevent and/or treat infections. Specific examples where microencapsulated antibiotics may prove useful include, soft-tissue wounds, following debridement and reduction or fixation of open fractures, to osteomyelitic bone after surgical debridement, after surgical insertion of prostheses such as hip/knee replacements (arthroplasty), and following vascular surgery or grafting.

4 Claims, 3 Drawing Sheets

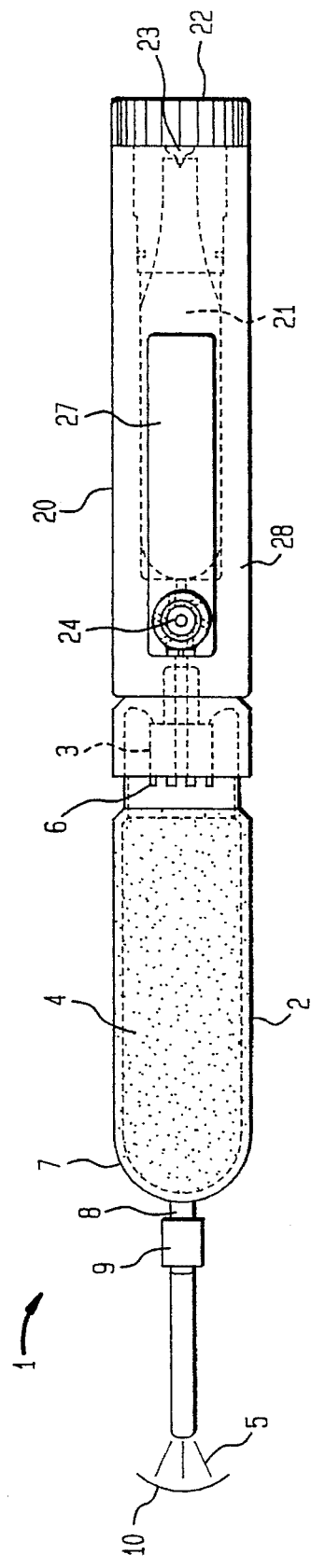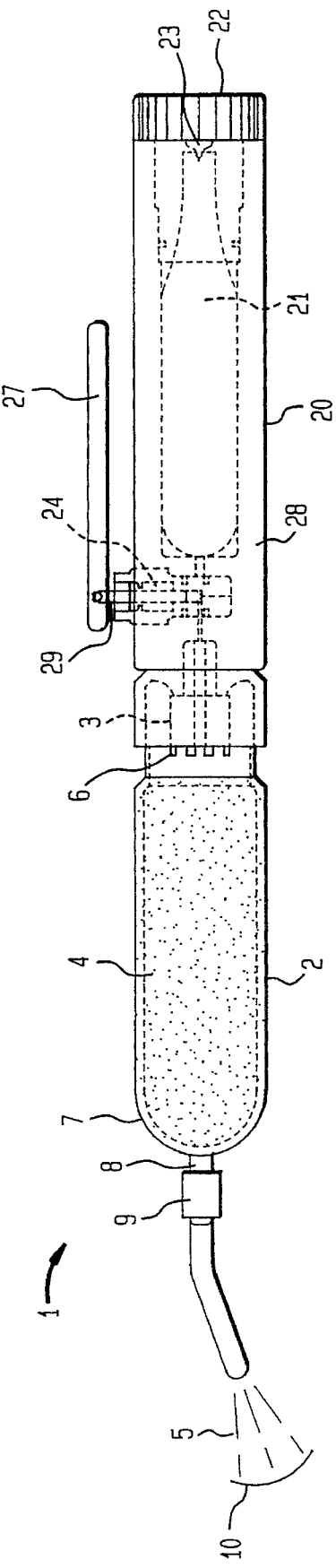

MICROSPHERE DRUG APPLICATION DEVICE

This application is a continuation-in-part of U.S. patent application Ser. No. 07/493,597, filed Mar. 15, 1990, now abandoned.

FIELD OF THE INVENTION

This invention relates to an apparatus and method for dispensing microencapsulated medicinal compositions.

BACKGROUND OF THE INVENTION

Among the most difficult types of wounds to treat are those characterized by the presence of infection, devitalized tissue and/or foreign-body contamination. Currently systemic antibiotic therapy by intravenous or intramuscular injection is the clinically accepted standard for the prevention and treatment of infected surgical and traumatic wounds. Systemic administration of antibiotics is recognized as an inherently inefficient method for delivering drugs because only a small fraction of the total dose actually reaches the target area, and most of the drug is excreted unused. Additional drawbacks associated with systemic antibiotic therapy include; 1) the necessity to dose repeatedly at frequent intervals, 2) poor penetration of the antibiotic into ischemic tissue, 3) emergence of resistant bacterial strains from prolonged exposure to the drug, and 4) an increased risk of adverse side-effects because of the relatively high circulating levels of the drug. All of these disadvantages would be overcome by the development of a technique for delivering drugs directly to the target site in a form which will allow release of the drug over an extended time period. Since such a method would concentrate the drug directly where it is needed, only a small fraction of the dose would enter the systemic circulation of the patient.

Recently microencapsulated antibiotics have been developed. The local application of such encapsulated antibiotics to traumatic and surgical wounds has been described in copending U.S. patent application Ser. No. 07/493,597, filed Mar. 15, 1990, which is incorporated herein by reference in its entirety. The '597 patent application describes the preparation of antibiotics encapsulated in biodegradable polymers based on lactic and/or glycolic acids and their use. The patent application further describes methods for introducing microencapsulated antibiotics into wounds by either injecting microcapsules suspended in a carrier into the wound or by layering the microencapsulated antibiotics on the wound. For maximum effectiveness it is desirable or even essential for the microcapsules be distributed as evenly as possible in/on the wound site. Uneven drug distribution may result in treatment failure since some areas may remain untreated. Animal studies have shown that the efficacy of therapy with microencapsulated drugs is dependent to a large extent on the ability to achieve a uniform distribution of the microspheres throughout the wound site.

The injection route is suitable only for introducing material into the limited area which the needle can traverse. The layering technique has presented difficulties because the microcapsules have shown a tendency to clump, which has made it necessary to manually spread the capsules over the site. When the microspheres clump together it has been found to interfere with the desired timed release of the active agent. Shaker-type applicators, dispensing from pipets and other methods have not afforded an easy method for obtaining the required distribution.

It has become apparent that an easier and more accurate method is needed for implanting or spreading the microcapsules.

SUMMARY OF THE INVENTION

The present invention relates to apparatus and methods for dispensing medicinals encapsulated in a biodegradable polymer in surgical and other wounds. The apparatus, a microcapsule drug applicator (hereinafter "MDA") allows the caregiver to implant or spread measured and uniform quantities of microencapsulated medicinals in or on surgical or traumatic wounds to prevent and/or treat infections. Specific examples where microencapsulated antibiotics may prove useful include, but are not limited to, soft-tissue wounds, following debridement and reduction or fixation of open fractures, to osteomyelitic bone after surgical debridement, after surgical insertion of prostheses such as hip/knee replacements (arthroplasty), and following vascular surgery or grafting. In such cases infection is either already present or the risk of infection is high. Local implantation of microencapsulated antibiotics can provide a significantly higher local concentration of medication at the wound site than can be obtained using traditional systemic therapy, and offers the possibility of producing significantly reduced side effects. Consequently a significantly greater efficacy in preventing and/or eliminating infections can be achieved. In addition to antibiotics other drugs and biological agents may be encapsulated and administered in a similar fashion. Such medicinals include but are by no means limited to; 1) steroids, 2) narcotic antagonists, 3) local anesthetics, 4) growth factors, 5) anti-cancer agents and 6) non-steroidal anti-inflammatory drugs.

The vast majority of anti-cancer agents currently administered systemically are highly toxic and are associated with severe side-effects. Encapsulated cytotoxic agents may be implanted into a site following resection of a tumor. The sustained release of the drug may suppress or prevent recurrence of the primary tumor from cells left in the area and also prevent secondary spread to distant sites (metastasis). Since the action of the drug would be primarily limited to the target area, it would reduce or eliminate serious side-effects currently experienced with many anti-cancer drugs.

The MDA of the invention assists the care-giver with the logistical application of microspheres throughout the wound. As antibiotic is released from each of the multitude of individual microspheres "sprayed" into the area, the tissue becomes uniformly bathed in sustained high concentrations of the drug which are difficult to obtain and/or maintain by other methods of treatment. The MDA of the invention may also be used to deliver other encapsulated drugs such as anesthetics, hemostatic agents or anti-tumor drugs.

BRIEF DESCRIPTION OF THE DRAWINGS

FIG. 1 is a top view of the microsphere drug applicator of the invention with a compressed gas cartridge in the nebulizer.

FIG. 2 is a side view of the microsphere drug applicator of the invention with a compressed gas cartridge in the nebulizer.

FIG. 3 is a cross-sectional view of a sterile vial containing sterile microspheres.

FIG. 4 illustrates a cap for use on the nebulizer when an external gas source is used rather than a compressed gas cartridge.

DETAILED DESCRIPTION OF THE INVENTION

Figure 3:
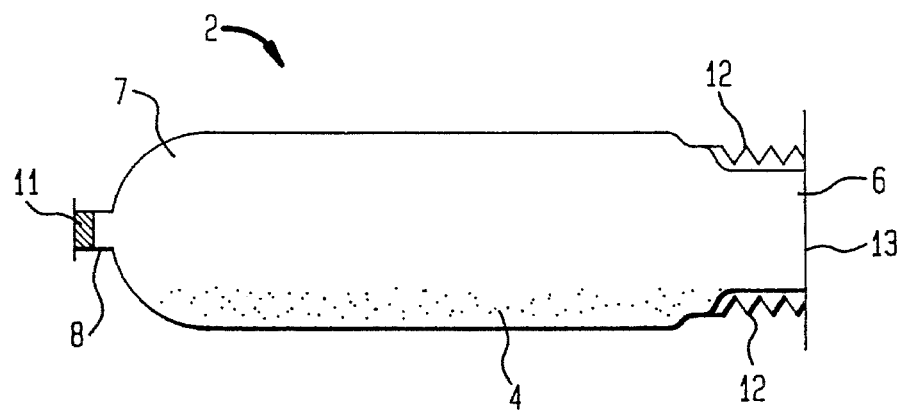

Referring to FIGS. 1 and 2, the microsphere drug applicator (MDA) 1 of the invention comprises two basic units, a drug container or vial 2 to contain the microspheres and a nebulizer unit 20 which generates a nebulizing gas stream required to spray or propel microspheres 4 contained in the vial 2 into or onto the area to be treated 10 as stream 5. The drawings and description of an MDA used in this disclosure are intended merely to assist in visualization of the principles employed in the invention and should not be interpreted as limiting the invention in any way or in particular to the embodiment illustrated. A variety of designs may be employed for the apparatus of the invention utilizing variations of the illustrative example using methods well-understood in the art. Factors which must be taken into account in the design of a specific MDA include 1) an ability to deliver microspheres uniformly over a given area, 2) an ability to adjust or throttle the flow rate of the propelling gas in order to be able to deliver microspheres of different sizes successfully, 3) ease of use by the care-giver, 4) overall cost of production, 5) simplicity , 6) portability, and (7) ability to sterilize the device.

Figure 7:
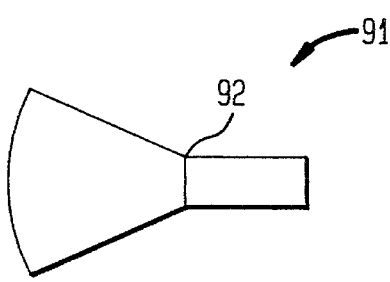
FIG. 7 is a view of a (swivel) nozzle useful in the practice of the invention.

Referring to FIG. 3, the drug container or vial 2 preferably is made of a reasonably clear plastic such as a polycarbonate, polyester such as polyethylene terephthalate, polystyrene, high-density polyethylene, polypropylene or the like in order to allow visualization of the encapsulated drug or medicinal microspheres 4 it contains. The plastic should be selected so as to be able to withstand sterilization with heat or ethylene oxide or other method well-known in the art. Less preferably the vial 2 may be made of metal, such as stainless steel or aluminum. In a preferred form of the invention the vial 2 will contain a known pre-weighed amount of a sterile encapsulated drug 4 prefilled by the manufacturer, although a sterile vial may be filled with sterile contents under antiseptic conditions at or about the time of use. The vial 2 must be large enough to allow creation of an air vortex to circulate the length of the vial 2 starting at the point 6 where air enters the vial 2 from the attached nebulizer 20 (see FIGS. 1 and 2). The air to microsphere ratio must be in the range of at least about 5–10:1, the ratio depending on the size of the microspheres 4 to be delivered. The exit area 7 should be rounded, preferably to a substantially full radius, i.e. hemispherical, in order to ensure complete delivery of the microspheres from the vial. If the end is not fully rounded delivering the microspheres may be difficult or impossible. At the exit of the vial 2 there is a nozzle end 8 to direct the flow 5 to the treatment area 10 (see FIGS. 1 and 2) or preferably, as shown in FIGS. 1 and 2, which can accept a variety of special-purpose nozzles 9 (shown in FIGS. 1 and 2) attachable to nozzle end 8 by a snap-on fitting, screw thread or the like, which are designed to spray the microspheres 4 in the desired or necessary pattern for the particular occasion. Particularly preferred for many uses is a "wing-tip" nozzle 91 capable of generating a spread pattern and preferably capable of rotating 360° about swivel 92 (FIG. 7). If the vial 2 has been prefilled with microspheres 4 the nozzle 8 is sealed with seal 11 to preserve the sterility of the tip of nozzle e and the contents of vial 2. The seal 11 may be an easily removable pull-tab stopper or the like, the design of which should protect the tip and contents but is not otherwise critical. A similar pull-tab stopper 13 is needed for inlet 6 when units are not preassembled. The inlet 6 for nebulizing gas is at the opposite end of the vial 2. The inlet end is provided with joining means including but not limited to screw threads 12 as illustrated or alternatively a Luer-lock or equivalent system for attaching the nebulizer 20 (see FIG. 1 and 2). When the vial 2 has been prefilled with microspheres 4 the inlet end of the vial should be closed with a sterile pull-tab foil 13 to contain the microspheres and maintain the sterility of the endpiece and the contents of the vial 2. In order to maximize sterility prefilled vials are preferably further enclosed by the manufacturer in a sterile package which can be opened at the time of use.

Figure 4:
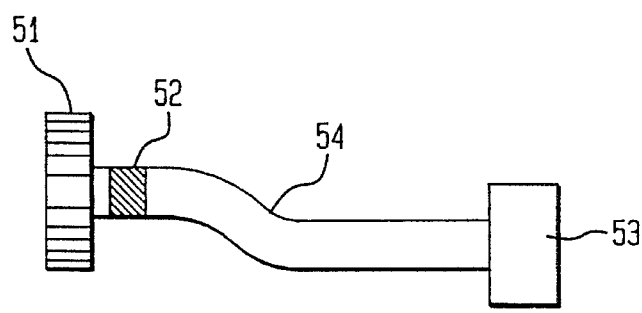

Referring again to FIGS. 1 and 2, the shell of the nebulizer unit 20 preferably is made of a light-weight metal such as aluminum which has sufficient strength to withstand the gas pressure used to activate the system. The gas should be a reasonably unreactive non-toxic gas such as air, nitrogen, carbon dioxide and the like. The pressure of the gas used to nebulize the microspheres is not critical, and may range from as little as that of a puff of breath (a few inches of water) to as much as 900 psi or more. There is no need to use gas at a very high pressure since the MDA would then have to be made of higher strength materials. Sources of gas for driving the system include, but are not limited to, small self-contained gas cylinders 21 such as the 12 gram Powerlet® (Crossman) designed for airguns, filled with sterile gas, useful under field conditions, or an external source of sterile compressed gas such as is generally available in an operating theater which may be attached to the nebulizer 20 with a quick-connect fitting of the kind well-known to the art (FIG. 4). A screw-on cap 22 held by screw threads at the end of the nebulizer 20 and equipped with a metal point 23 which punctures the end of the gas cylinder 21 when the cap is screwed on is particularly convenient. When an external gas source is used a cap 51 (FIG. 4) having a quick-connect fitting 52 may be substituted for the cap 22.

Figure 5:
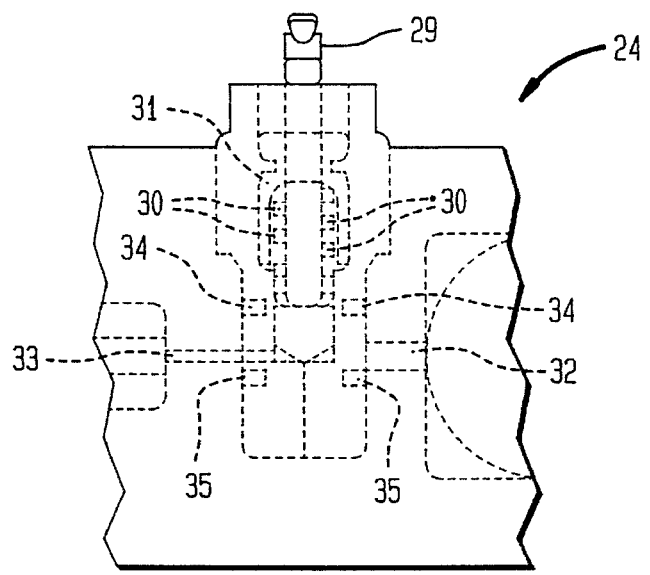
FIG. 5 is a view of a needle valve mechanism useful in the practice of the invention.

Referring to FIGS. 1 and 2, a valve 24 which affords precise control of gas flow such as a needle valve or its equivalent is critical for operating the system. A typical needle valve is shown in detail in FIG. 5. The openings 32 and 33 for the flow of gas must be large enough to allow a flow of gas sufficient to nebulize the microspheres 4, but afford sufficient control to allow control of the pressure required to ensure a relatively uniform vortex action in the vial 2. A convenient method for attaining good control is a lever 27 attached to the nebulizer 20 which activates the stylus 29 by a simple squeezing motion by the operator. In this embodiment the stylus 29 and valve plug 31 are biased by spring 30 in the closed position (down, not shown) so that when the lever 27 is depressed the plug 31 attached to stylus 29 is moved (up) out of the path between inlet 32 and outlet 33 as shown in FIG. 5. It is particularly important that the O-rings 34 and 35 fit tightly against the body 31 when in the closed position in order to prevent leakage of (high pressure) gas when the valve is closed. When the lever 27 is activated the stylus 29 rises in proportion to the degree to which the lever 27 has been depressed, allowing gas to flow from the nebulizer chamber 28 through the vortex valve 3 and into the drug vial 2. The lever and needle valve provide the control required to finely adjust the gas stream required to aerosolize microspheres of varying sizes, ranging from less than 45 to 250μ or more. Other equivalent means for controlling gas flow will be evident to those skilled in the art. The vortex valve 3 is attached to the discharge end of the nebulizer 20. It is convenient to equip the discharge end of the nebulizer with screw threads or a Luer-lock or the like to mate with the corresponding threads or lock 12 (see FIG. 3) of the vial 2 to allow simple assembly of the apparatus.

Figure 6A:
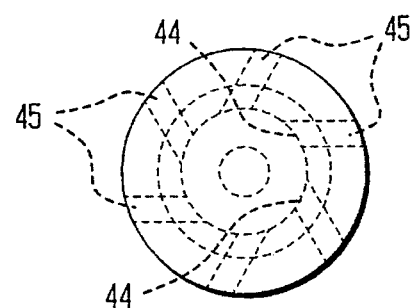
FIGS. 6A and 6B are views of a vortex valve useful for practice of the invention.
Figure 6B:
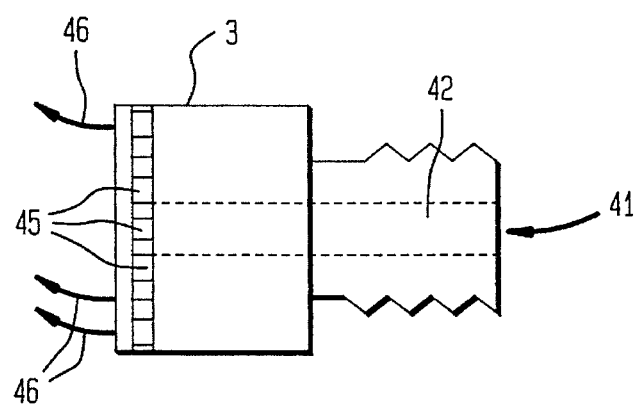

Referring to FIGS. 6A and 6B, the vortex valve 3 is activated by gas pressure. The flow of gas 41 through the tubular opening 42 in the body of the vortex valve is divided into multiple openings wherein the exit 45 of each opening is displaced radially from its entrance 44 thus creating a vortex in the exiting gas flow 46.

The entire nebulizer unit 20, needle valve 24, and vortex valve 3 and their constituent parts should be made of materials which can be sterilized before each use by means well-known to the art such as heat or chemical sterilization with ethylene 8 when the nebulizer unit is sterile the opening 47 should be protected with a pull-cap 48 or similar means to maintain the nebulizer unit in a sterile condition until it is used.

Figure 8:
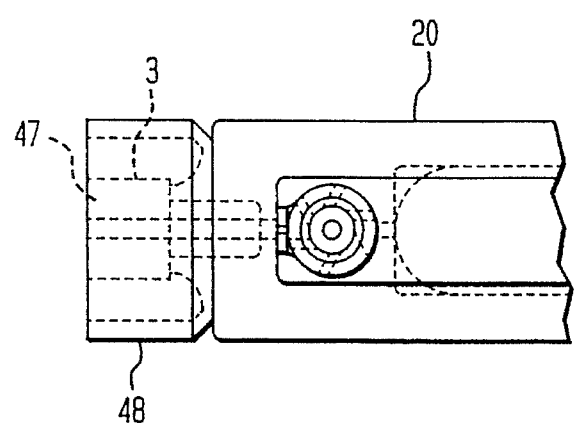
FIG. 8 illustrates the exit end of the nebulizer with a protective seal in place over the exit.

The operation of the MDA is as follows. Referring to FIGS. 1, 2 and 3 the care giver removes protective seal 13 (FIG. 3) from the vial 2 and the protective seal 48 (FIG. 8) from nebulizer unit 20 and attaches the nebulizer to the vial using the screw threads or Luer lock 12 (FIG. 3). The protective seal 11 is removed from the nozzle end of the vial 2 and a nozzle 9 or 91 is attached to the vial at the nozzle end 8. If a self-contained gas source is to be used, the end cap 22 is screwed down to cause the point 23 to pierce the seal of the gas cylinder 21, or if an external gas source is to be used end cap 51 is used and gas source 53 is connected by line 54 which is attached using the quick-connect fitting 52. The MDA is now ready for use by the caregiver.

The MDA is held by the caregiver in a manner which allows him or her to exert whatever pressure is needed on lever 27 while aiming the nozzle 8, 9 or 91 at the surface 10. Pressing on the lever 27 causes the needle valve 24 to open. The more lever 27 is depressed by the caregiver the more the body 31 of the needle valve is moved from the passage 32–33 allowing control of the gas flow from the gas chamber 28 through the passage 32–33 through the vortex valve 1 and into the vial 2 at the opening 6. The swirling gas flow entering the vial 2 nebulizes the microspheres 4 and blows the nebulized spheres through the nozzle as stream 5 onto the wound surface 10. When the proper amount of microspheres has been placed on the wound the caregiver releases lever 27, whereupon the flow stops. These steps may be repeated if necessary until the microspheres have been deposited in the area to be treated in the desired amount.

In general, vials are discarded after use, and the nebulizer unit is (re)sterilized by heat or chemical sterilization before being used again.

We claim:

1. An apparatus for dispensing microencapsulated medicinals which comprises a vial to contain the microencapsulated medicinal having an entrance end having a gas entrance opening and a nozzle end having an exit opening, each opening having attachment means, the nozzle end of the vial being substantially hemispherical, and a nebulizer unit comprising a gas chamber having an exit opening, a needle valve having an entrance opening and an exit opening having attachment means, means for activating the needle valve, and a vortex valve having an entrance opening and an exit opening having attachment means, assembled by attaching the exit opening of the nebulizer to the entrance end of the needle valve, the exit end of the needle valve to the entrance end of the vortex valve and the exit end of the vortex valve to the vial in a manner such that when the needle valve is opened gas from a gas source flows from the gas chamber through the vortex valve and into the vial to nebulize the contained microencapsulated medicinal and dispense it through the nozzle end of the vial.

2. An apparatus of claim 1 in which a special purpose nozzle has been attached to the nozzle opening.

3. A sterile nebulizer unit comprising a gas chamber, a needle valve, means for activating the needle valve, and a vortex valve having an exit opening which forms the exit opening of the nebulizer, assembled in a manner such that when the needle valve is opened gas from a gas source will flow from the gas chamber through the vortex valve to exit the nebulizer, the exit opening of the nebulizer being sealed with a removable seal.

4. A method for dispensing a microencapsulated medicinal on a surface which comprises a) attaching a vial containing the microencapsulated medicinal having an entrance end having a gas entrance opening and a nozzle end having an exit opening, each opening having attachment means, the nozzle end of the vial being substantially hemispherical, to a nebulizer unit comprising a gas chamber, a needle valve, means for activating the needle valve, and a vortex valve having an exit opening having attachment means which forms the exit opening of the nebulizer, assembled in a manner such that when a gas source is attached to the gas chamber when the needle valve is opened gas from the gas source will flow from the gas chamber through the needle valve and then the vortex valve; by attaching the exit opening of the nebulizer to the entrance end of the vial, and then b) activating the needle valve and dispensing the microencapsulated medicinal.

\* \* \* \* \*